United States Patent [19]

Kojima et al.

[11] Patent Number: 4,523,806
[45] Date of Patent: Jun. 18, 1985

[54] METHOD AND APPARATUS FOR RESTORING THE LIGHT TRANSMITTANCE OF AN IMAGE-TRANSMITTING OPTICAL FIBER BUNDLE USED IN A FIBER OPTIC ENDOSCOPE

[75] Inventors: Takuo Kojima; Kuniaki Ishibashi, both of Saitama, Japan

[73] Assignee: Fuji Photo Optical Co., Ltd., Saitama, Japan

[21] Appl. No.: 349,619

[22] Filed: Feb. 17, 1982

[30] Foreign Application Priority Data

Feb. 17, 1981 [JP] Japan ................................ 56-22082
Jan. 20, 1982 [JP] Japan ................................ 57-005907

[51] Int. Cl.³ .............................................. G02B 5/14
[52] U.S. Cl. ............................... 350/96.25; 250/492.1
[58] Field of Search .................... 350/96.25; 250/492.1

[56] References Cited

U.S. PATENT DOCUMENTS 4,232,228  11/1980  Reich et al. ..................... 250/492.1
4,375,315   3/1983  Lacombat et al. ............... 350/96.25

Primary Examiner—William L. Sikes
Assistant Examiner—Robert E. Wise
Attorney, Agent, or Firm—Young & Thompson

[57] ABSTRACT

When a fiber optic endoscope is exposed to X-ray or γ-ray irradiation, the fiber bundle becomes discolored and there is thus a reduction in light transmittance. This makes observation or examination difficult or impossible. The irradiation-induced reduction in light transmittance of the image transmitting fiber bundle is restored, according to this invention, by visible light radiation endwise therethrough. Visible light radiation having a short wavelength largely restore the light transmittance to that before irradiation in a short period of time.

3 Claims, 10 Drawing Figures

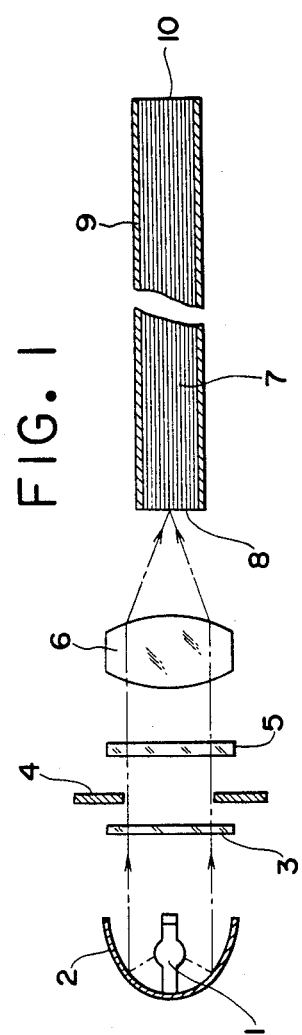
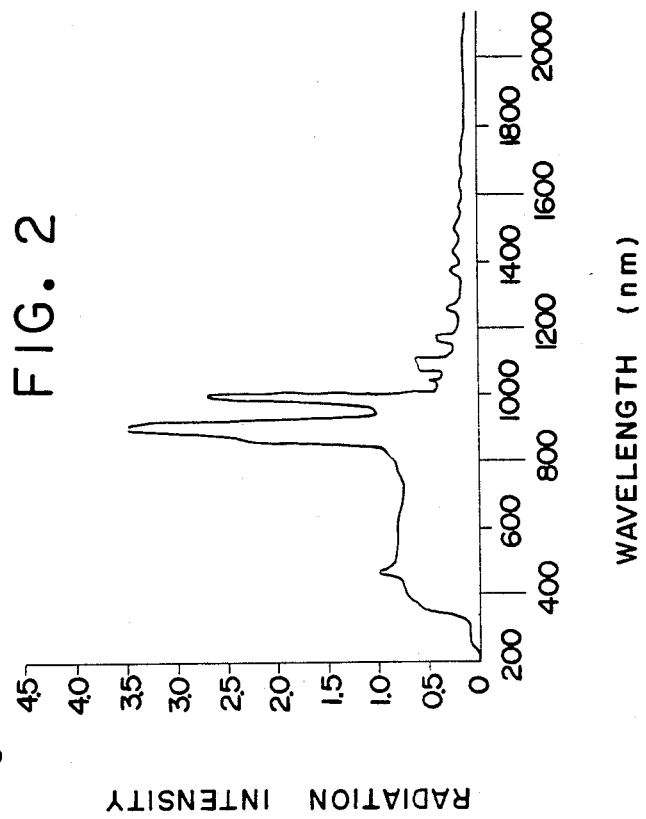

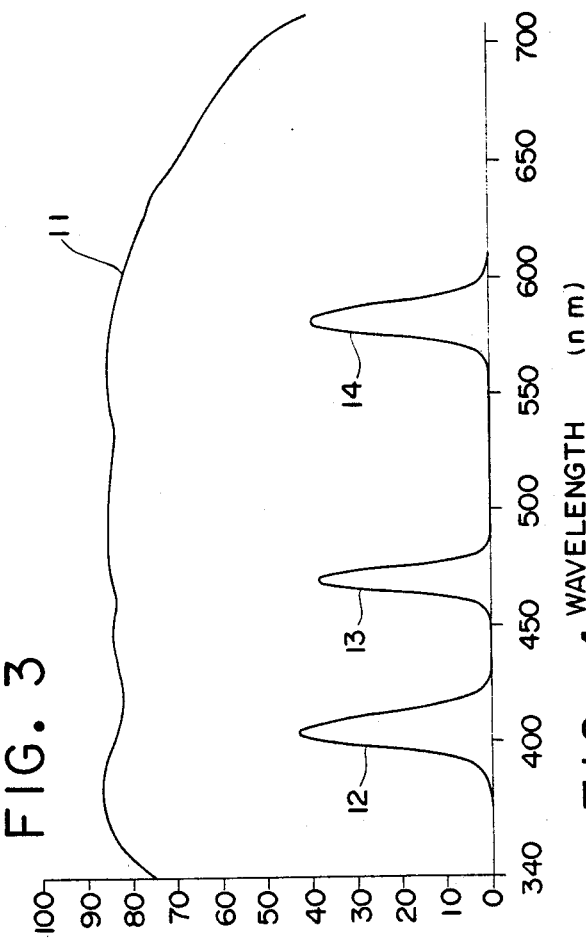
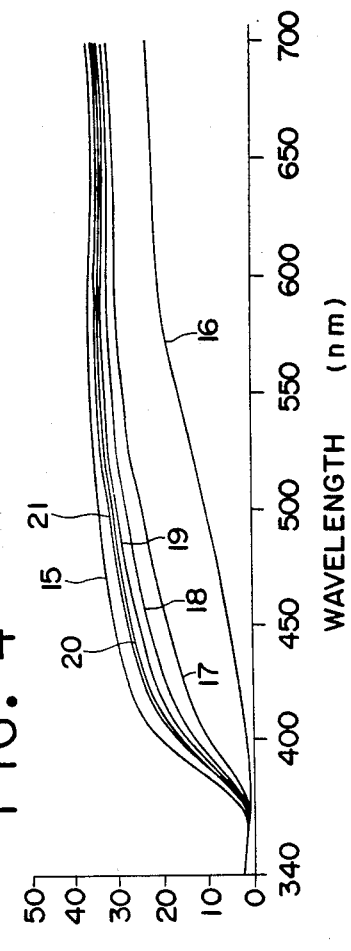
FIG. 3
FIG. 4

METHOD AND APPARATUS FOR RESTORING THE LIGHT TRANSMITTANCE OF AN IMAGE-TRANSMITTING OPTICAL FIBER BUNDLE USED IN A FIBER OPTIC ENDOSCOPE

BACKGROUND OF THE INVENTION

The present invention relates to methods and apparatus for restoring the reduced light transmittance of an image-transmitting optical fiber bundle, which reduction results from X-ray or γ-ray irradiation, and for thus making it once more usable for performing observations or examinations.

Fiber optic endoscopes are widely used for the purpose of observing or examining inaccessible cavities of a body which are impossible to observe or examine directly from the outside, and are generally divided into two categories, i.e., medical and industrial. Fiber optic endoscopes for medical use are used to observe or examine cavities of a human body such as the stomach, the duodenum, the colon, and the like; whilst the industrial are used to observe or examine the internal parts of machinery such as engines, nuclear reactors and the like. These fiber optic endoscopes comprise optical fiber bundles, one for transmitting an image of the internal parts to be observed or examined and the other for transmitting illumination from the outside. Each of said optical fiber bundles comprises an extremely large number of optical fibers with their opposite end portions cemented together and the major portion between the ends free to move relative to each other so as to be flexible, thereby to be insertable along a tortuous passage of a body.

Upon inserting a fiber optic endoscope into a human body, a fluoroscopic observation is often taken to locate accurately an inserted position of the top thereof relative to a region within the human body so as to ensure the safety of the person under examination. A certain fiber optic endoscope for medical use, for instance a duodenum endoscope, can be utilized for the purpose of endoscopic retrograde cholangiopancreatography (ERCP) examinations wherein a contrast medium is, for a fluoroscopic observation, injected into the pancreatic and bile ducts through a tube which is inserted in a therapeutic instrument guide channel of a fiber optic endoscope. As described above, fiber optic endoscopes for medical use have many uses in connection with fluoroscopic observation. As a result, an optical fiber bundle is frequently exposed to irradiation through a protective rubber tube.

Generally, the exposure of optical glass to X-ray or γ-ray irradiation induces coloration thereof and thus decreases its light transmittance. According to published reports, the irradiation-induced coloration is due to so-called color centers. Irradiation interacts with the electrons of the atoms of the molecules of glass to release them. The released electrons impinge upon the electrons of other atoms to release them also. As a result, positive holes are formed having positive charges. Although a large number of released electrons are recombined with positive holes, the remaining released electrons are partially bound to structural imperfections of the optical glass to form such color centers. Because these electrons and positive holes at the color centers are weakly bound, glass absorbs light with a wavelength greater than the fundamental absorption band of the crystal before irradiation, to form another fundamental absorption band in the range of wavelengths of visible light.

The irradiation-induced coloration of glass is unavoidable in an image transmitting optical fiber bundle having thousands to tens of thousands of glass fibers each of which is composed of a fiber core and fiber cladding and has a diameter of the order of microns. An optical fiber bundle used in a fiber optic endoscope is frequently exposed to irradiation and thus suffers an increase in its absorption of light having a wavelength 400 to 550 nm, and so becomes colored yellowish brown. The yellowish-brown coloration appears in a fiber bundle within a protective tube after irradiation by a certain number of Roentgens (R) and deepens with further exposure. A fiber optic endoscope having an image-transmitting fiber bundle with such irradiation-induced coloration may be unacceptable for observing or examining an image therethrough and so may be returned to the manufacturer to replace the image-transmitting fiber bundle. But an image-transmitting fiber bundle is very expensive; and moreover, the replacement thereof is extremely complex and hence very costly.

To prevent optical glass from becoming colored yellow, it is known to mix cerium oxide in the composition of the glass. But since a cerium-oxide-containing glass has a tinge of yellow itself, this decreases its light transmittance. Optical elements such as optical lenses, prisms and the like, which are thin in the direction of the optical path, have substantially no effect on observations therethrough even if a decline of light transmittance is suffered; but a long optical fiber of diameter 10 to 50 microns and overall length 700 to 1200 mm is influenced considerably owing to marked degradation of the light passing therethrough. For this reason, image-transmitting glass fiber bundles conventionally used are made of glass without cerium oxide.

Another alternative for preventing irradiation-induced coloration of a glass fiber bundle is disclosed in Japanese Utility Model Publication No. 53-43025, in which an image-transmitting fiber bundle is inserted through a sheath of a concentric helix of metal strip covered with an irradiation-shielding layer of material such as lead, cerium or the like. This has the advantage that the sheath can prevent the image-transmitting fiber bundle from being exposed to excessive irradiation. However, coloration may still be induced by irradiation through gaps between the helical turns of the metal strip.

We obtained empirically the result that the fading of a colored image-transmitting fiber bundle induced by irradiation could be caused by visible light radiation, and then, the light transmittance thereof was recovered to a degree acceptable for performing observations and examinations.

OBJECTS OF THE INVENTION

Therefore, the principal object of the present invention is to provide a method of and apparatus for restoring the light transmittance of an image-transmitting optical fiber bundle colored yellow.

Another object of the present invention is to provide a method of and apparatus for restoring the light transmittance of an image-transmitting fiber bundle close to what it was before irradiation, and in a short time.

Still another object of the present invention is to provide a method of and apparatus for restoring a light-transmitting fiber bundle, which will be easy to perform and low in cost.

A further object of the present invention is to provide apparatus for restoring the light transmittance of an image-transmitting fiber bundle, which will be simple in structure.

SUMMARY OF THE INVENTION

These and other objects of the present invention are achieved by exposing the end of a yellow-colored image-transmitting fiber bundle, whose light transmittance has thus been lowered, to visible light radiation. Either the front end or the rear end of the image-transmitting fiber bundle may be exposed to visible light radiation. Furthermore, the end may be exposed to visible light radiation through either an ocular assembly on the front end of the fiber bundle or an objective assembly on the rear end of the fiber bundle.

The apparatus embodying the present invention is adapted to expose one end of an image-transmitting fiber bundle to visible light radiated from a light source which is arranged to optically face to that end. An arrangement in which the visible light source is aligned with the end of the image-transmitting fiber bundle is preferred. In the case of a relatively great distance between the light source and the end of the image-transmitting fiber bundle, it is advantageous to provide a mirror for changing the direction of the light path between the light source and the end of the image-transmitting fiber bundle, for the purpose of miniaturizing the assembly.

The longer the visible light radiating time is, the higher the degree of recovery in light transmittance of the image-transmitting fiber bundle is. Moreover, at a fixed level of visible light radiation, the higher the radiation density is, the greater is the recovery of light transmittance. Furthermore, visible light of short wavelength is significantly more effective to restore light transmittance; and in this way a light transmittance nearly that of the original can be regained in a short time. Thus, visible light of short wavelength and high radiation density is preferred.

BRIEF DESCRIPTION OF THE DRAWINGS

Other objects, advantages and features of novelty of the invention will be evident to those skilled in the art from a consideration of the following description, taken in conjunction with the accompanying drawings, in which:

FIG. 1 is a schematic view of experimental apparatus for practicing the present invention;

FIG. 2 is a graph showing radiation density of a xenon lamp;

FIG. 3 is a graph showing spectral transmittance factors of a heat-absorbing filter and an interference filter;

FIG. 4 is a graph showing changes in the spectral transmittance factor of an image-transmitting fiber bundle using an interference filter having a mean or peak wavelength of 404 nm;

DETAILED DESCRIPTION OF THE INVENTION

Figure 5:
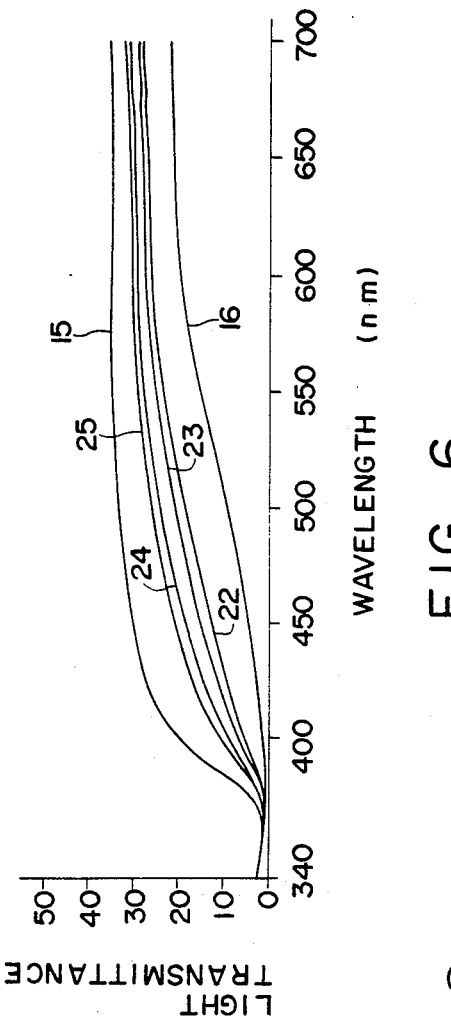
FIG. 5 is a graph showing changes in the spectral transmittance factor of an image-transmitting fiber bundle using an interference filter having a mean or peak wavelength of 470 nm.

Referring now in detail to the drawings, the apparatus illustrated in FIG. 1 was used to carry out experimental measurements of correlations between wavelength and fading of color of an image-transmitting fiber bundle of a fiber optic endoscope induced by irradiation. In FIG. 1, light emitted from a xenon lamp 1 is reflected by a parabolic mirror 2 to be directed forward upon a heat absorbing filter 3. Light passed through the heat absorbing filter 3 falls upon a condenser lens or condenser lens assembly 6 through a stop 4 with an aperture of 28 mm and an interference filter 5. The condenser lens assembly 6 causes the light to converge onto an end surface 8 of an optical fiber bundle 7 comprising an extremely large number of optical fibers each of diameter about 10 to 20 $\mu$m. The optical fiber bundle 7 to be measured is identical with the other one used for an image transmitting fiber bundle of fiber optic endoscope in every respect. That is to say, both ends of the optical fiber bundle 7 are in the form of a square with one side of 2 mm and the bundle has an overall length of 1250 mm. The optical fibers at both ends, to the extent of about 10 mm of the length of fiber bundle 7, are rigidly secured together by an adhesive such as epoxy resin so as to maintain their spatial relationship; but they are free along their extent between the ends so as to be flexible or freely relatively movable. The fiber bundle 7 is covered by a rubber tube 9 for protection.

The fiber bundle 7 has been exposed, from its exit end 10 to about 300 mm away therefrom, to 90R irradiation by an X-ray tube operating at 85 KVp and 300 mA, and thus has become colored yellow.

FIG. 2 shows the radiation density of a xenon lamp. The xenon lamp 1 has a density characteristic which is substantially flat in the range of visible light of wavelength 380 to 780 nm.

FIG. 3 shows the spectral transmittance factors of a heat-absorbing filter and an interference filter. The heat-absorbing filter 3, which has a spectral transmittance factor represented by the curve 11, removes heat rays from radiation emitted by the xenon lamp 1. The heat-absorbing filter 3 serves to prevent the epoxy resin used as adhesive for rigidly securing together the fibers at the end portions thereof, from blackening upon heating of the epoxy resin higher than its heat-resisting temperature of about 80° to 100° C. Differences in spectral transmittance factors of the fiber bundle 7 experimentally obtained after visible light radiation with selective use of interference filter 5 are shown by the curves of FIGS. 4 to 6, the filters having their means or peak wavelengths at 404 nm, 470 nm and 582 nm as shown by characteristic curves 12, 13 and 14 in FIG. 3, respectively.

FIG. 4 shows the differences in spectral transmittance factors of a fiber bundle 7 experimentally obtained after visible light radiation for various periods of time through an interference filter having its mean or peak wavelength at 404 nm, in the apparatus shown in FIG. 1. The curve 15 in FIG. 4 represents the spectral transmittance factor of the fiber bundle 7 before X-ray irradiation, and the curve 16 represents the same after the fiber bundle 7, from the light exit end 10 to about 300 mm away therefrom, has been irradiated by X-rays of 90R and has become colored yellow. The fiber bundle 7 having its spectral transmittance factor reduced to that shown by the curve 16 was, at its end 8, radiated with visible light through an interference filter having its mean or peak wavelength 404 nm for a quarter of an hour, for half an hour, for an hour, for two hours and for four hours, with the result that the recovery of spectral transmittance factor of the fiber bundle 7 represented by curves 17 to 21, respectively, was achieved.

FIG. 5 shows the differences in spectral transmittance factors of a fiber bundle 7 experimentally obtained after visible light radiation for various periods of time through an interference filter having its mean or peak wavelength at 470 nm. The curves 22 to 25 represent spectral transmittance factors of the fiber bundle 7 achieved after visibile light radiation for a quarter of an hour, for half an hour, for an hour and for two hours, respectively. The curves 15 and 16 represent the spectral transmittance factors of the fiber bundle before and after X-ray irradiation, respectively, in the same manner as shown in the curves 15 and 16 in FIG. 4.

Figure 6:
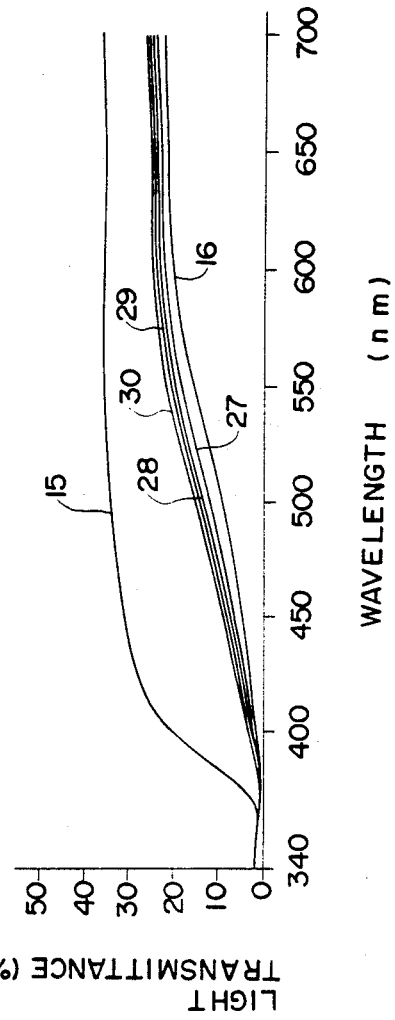
FIG. 6 is a graph showing changes in the spectral transmittance factor of an image-transmitting fiber bundle using an interference filter having a mean or peak wavelength of 582 nm.

FIG. 6 shows the differences in spectral transmittance factors of a fiber bundle 7 experimentally obtained after visible light radiation through an interference filter having its mean or peak wavelength at 582 nm. The curves 27 to 30 represent spectral transmittance factors of the fiber bundle achieved after visible light radiation for a quarter of an hour, for half an hour, for an hour and for two hours, respectively.

Figure 7:
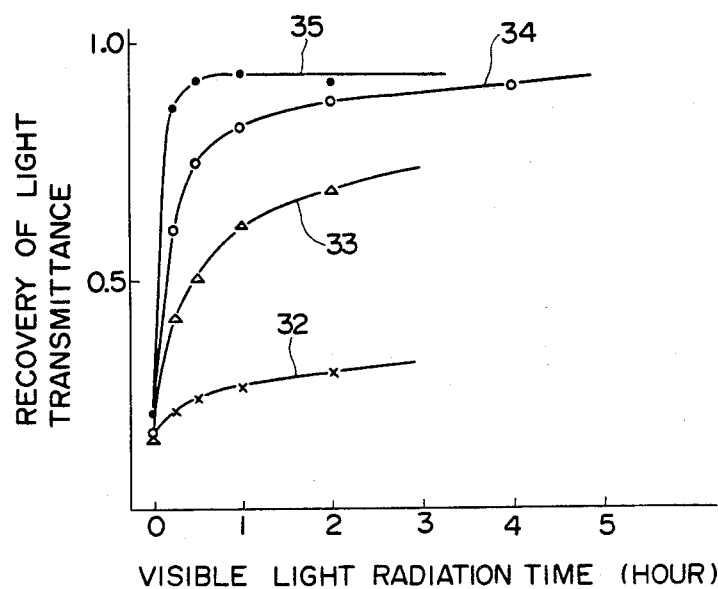
FIG. 7 is a graph of degree of recovery of spectral transmittance factor at a wavelength of 450 nm, versus visible light radiation time.

FIG. 7 shows the rate of recovery of light transmittance of a fiber bundle 7, as curves obtained by plotting the experimental values observed at a wavelength of 435 nm. Curves 32 to 34 show such recovery of light transmittance at a wavelength of 435 nm of the fiber bundle 7, in the case of using interference filters having their mean or peak wavelengths at 582 nm, 470 nm and 404 nm, respectively, and curve 35 is without any interference filter. In FIG. 7, the recovery of light transmittance plotted on the ordinate represents the rate of light transmittance recovered, relative to that before X-ray irradiation. From a study of FIG. 7, it seems quite probable that visible light radiation of about 650 nm wavelength will have the effect of causing the fiber bundle 7 to recover its light transmittance and that the shorter the wavelength of visible light radiation used, the faster the recovery of light transmittance of the fiber bundle 7. Furthermore, it will be apparent from FIG. 7 that the recovery of light transmittance of the fiber bundle 7 increases in rate in the range of about 500 to 470 nm in wavelength and becomes extremely large in the range of about 400 to 380 nm wavelength. Consequently it is desirable to use visible light radiation containing short wavelength components for the most efficient restoration of the light transmittance of fiber bundles. On the other hand, the highest recovery in light transmittance will be obtained without using any interference filter. It is believed, as described hereinafter, that this is due to visible light radiation which is higher in density and contains short wavelength components in the range of 380 to 400 nm.

Figure 8:
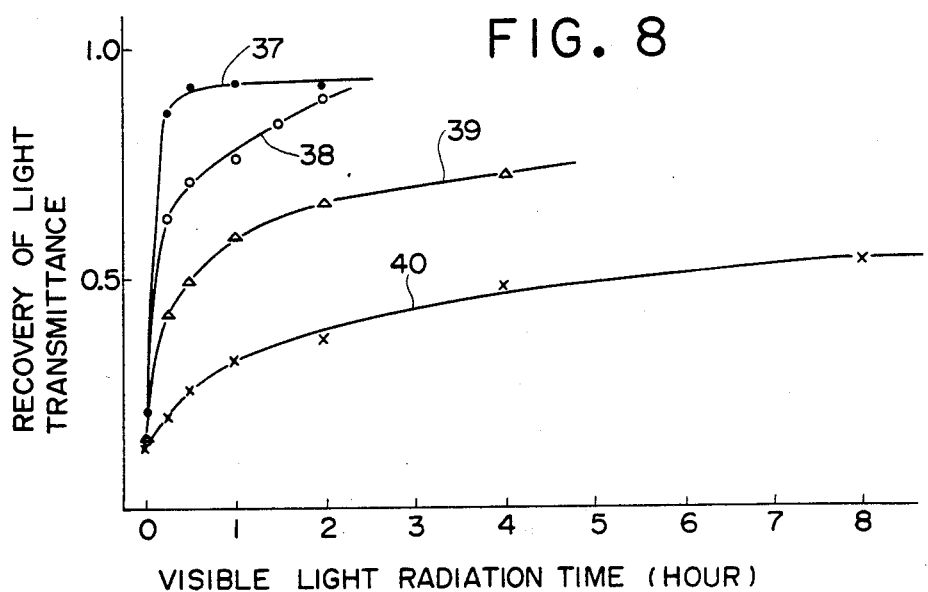
FIG. 8 is a graph of degree of recovery of spectral transmittance factor, versus visible light radiation time, for various amounts of radiations.

An experiment to investigate the dependence of recovery of light transmittance on radiation density was conducted with the apparatus shown in FIG. 1, by using neutral density (ND) filters instead of the interference filter 5. FIG. 8 shows the relationships between the recovery of light transmittance at 450 nm wavelength, and visible light radiation time, which were experimentally obtained. In FIG. 8, a characteristic curve 37 represents the recovery of light transmittance of a fiber bundle after visible light radiation without any ND filter. Characteristic curve 38 represents the recovery of light transmittance of a fiber bundle after visible light radiation reduced to a quarter of its total quantity of radiation using an ND filter of a density of four. Characteristic curve 39 represents the recovery of light transmittance of a fiber bundle after visible light radiation reduced to one sixteenth of the total quantity of radiation by using two ND filters of a density of four; and characteristic curve 40 represents the recovery of light transmittance after radiation reduced to 1/128 of the total quantity of radiation using two ND filters of a density of four and one ND filter of a density of eight. It will be apparent from FIG. 8 that the larger is the quantity of visible light radiation, the higher is the recovery of light transmittance.

Figure 9:
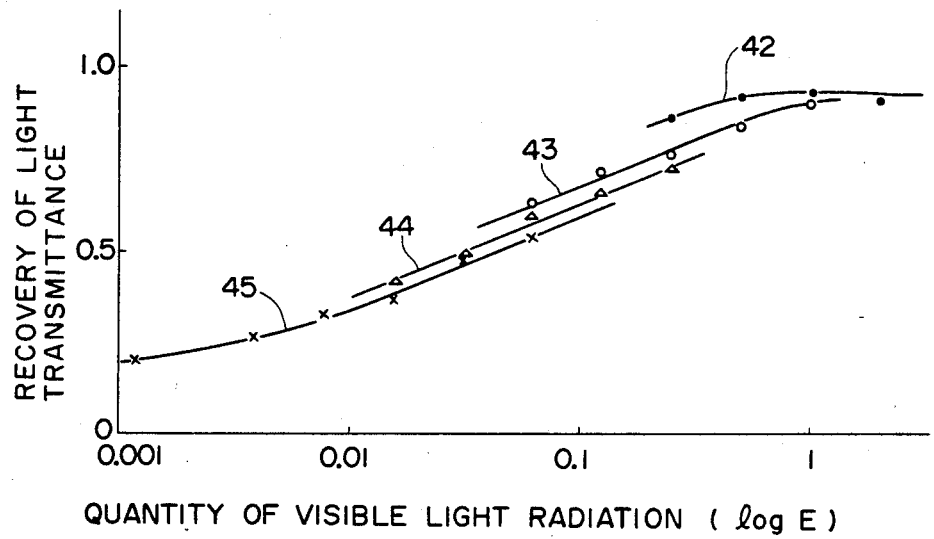
FIG. 9 is a graph of degree of recovery of spectral transmittance factor, versus quantity of visible light radiation.

FIG. 9 shows the relationship between the recovery of light transmittance of a fiber bundle and the quantity of visible light radiation (log E). In FIG. 9, characteristic curve 42 represents the recovery of light transmittance of a fiber bundle after visible light radiation without any filter. Characteristic curve 43 represents the recovery of light transmittance of a fiber bundle after visible radiation reduced to one fourth of the total quantity of radiation by using a filter. Characteristic curve 44 represents the recovery of transmittance after radiation is reduced to one sixteenth; and characteristic curve 45 represents the recovery of light transmittance after radiation is reduced to 1/128. It will be apparent from FIG. 9 that the rate of recovery of light transmittance is not proportional to the quantity of visible light radiation and that the larger is the quantity of visible light radiation, the higher is the recovery of light transmittance.

As a result of synthesizing data obtained experimentally, it is seen that a strong visible light, and a visible light short in wavelength, can act effectively for restoring light transmittance of a fiber bundle colored yellow.

Figure 10:
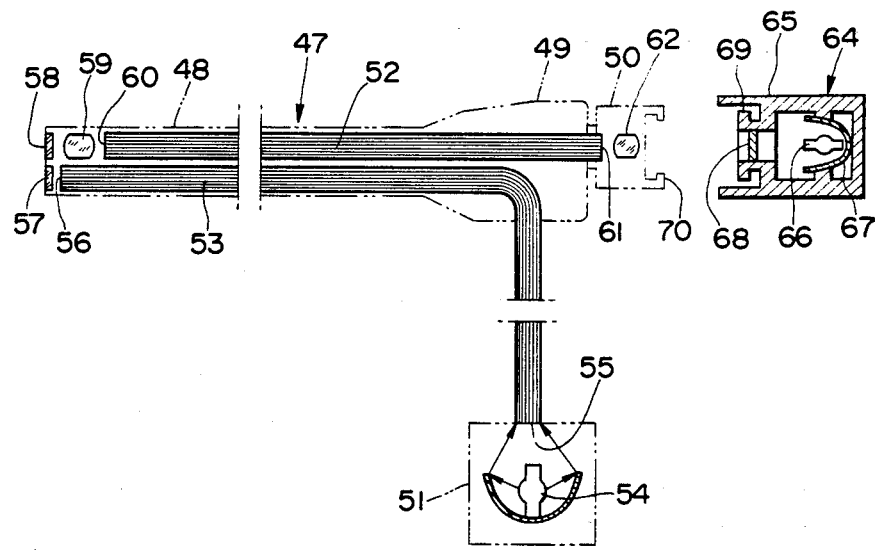
FIG. 10 is another schematic view of apparatus embodying the present invention.

FIG. 10 illustrates an embodiment of apparatus for restoring the light transmittance of a fiber bundle within a fiber optic endoscope. As is well known, a fiber optic endoscope 47 comprises an elongated flexible part 48 which is insertable into a body cavity to be examined, a remote control 49, an ocular part 50 and an illuminating light source 51, and includes an image-transmitting optical fiber bundle 42 and an illumination light transmitting optical fiber bundle 53 therein. The elongated flexible part 48 is, as is well known, adapted to be moved so as to look in any direction desired, by operating a control knob on the remote control part 49.

Light emitted from a light source 54 provided in the illuminating light source 51 is introduced into the light-transmitting optical fiber bundle 53 through its incident end 55 and exits therefrom through its exit end 56. This light then passes through a window 57 and illuminates the field to be examined or observed.

Reflected light from the observed field falls on the incident end 60 of the image-transmitting optical fiber bundle 52 through the window 58 and an objective assembly 59. An image on exit end 61 of the image-transmitting optical fiber bundle, which has been transmitted therethrough, can be observed through an ocular assembly 62 after magnification.

When the fiber optic endoscope 47 is used for fluoroscopy employing an X-ray monitoring TV, the actual dose received by the fiber bundle within the flexible part 48 is about 0.1R per examination. The light transmittance of the image-transmitting optical fiber bundle is gradually reduced by the yellow discoloration thereof and consequently the image-transmitting optical fiber bundle becomes unacceptable for continued use after a total dose of about 24R. Therefore, it is desirable to restore the light transmittance of the image-transmitting optical fiber bundle after a total dose received, for instance, of about 1.0R by using a light transmittance restoration apparatus as shown at 64.

The light transmittance restoration apparatus 64 comprises a light source 66 emitting radiation containing visible light with short wavelength, a reflecting mirror 67 and a heat absorbing filter 68 in a casing 65 and is adapted to be detachably connected to the ocular part 50. The connecting means is comprised by a bayonet mount with which casing 65 is provided. The bayonet mount has bayonet lugs 69 engageable with complementary bayonet lugs 70 of the ocular part 50 which are already present for mounting a camera or the like thereon.

A xenon lamp, a halogen lamp, a metal halogen lamp or the like may be employed as the light source 66. On the other hand, the illuminating light source 51 can be used as the light transmittance restoration apparatus; and in this case, the illuminating light source 51 is detachably connected to the ocular part 50, for example through a detachable mounting means (not shown).

What is claimed is:

1. A method of maintaining the light transmittance of an image-transmitting optical fiber bundle which has been exposed to X-ray irradiation, which comprises exposing said image-transmitting optical fiber bundle through one end to visible light radiation when the bundle has received about one roentgen unit of X-ray irradiation.

2. A method as claimed in claim 1, in which said bundle in normal use has an X-ray entry end and an X-ray exit end, and exposing said bundle to said visible light radiation through said exit end.

3. A method as claimed in claim 1, and passing said visible light radiation through a heat-absorbing filter disposed between the source of said visible light radiation and said one end of said bundle.

* * * * *